Figure 3:
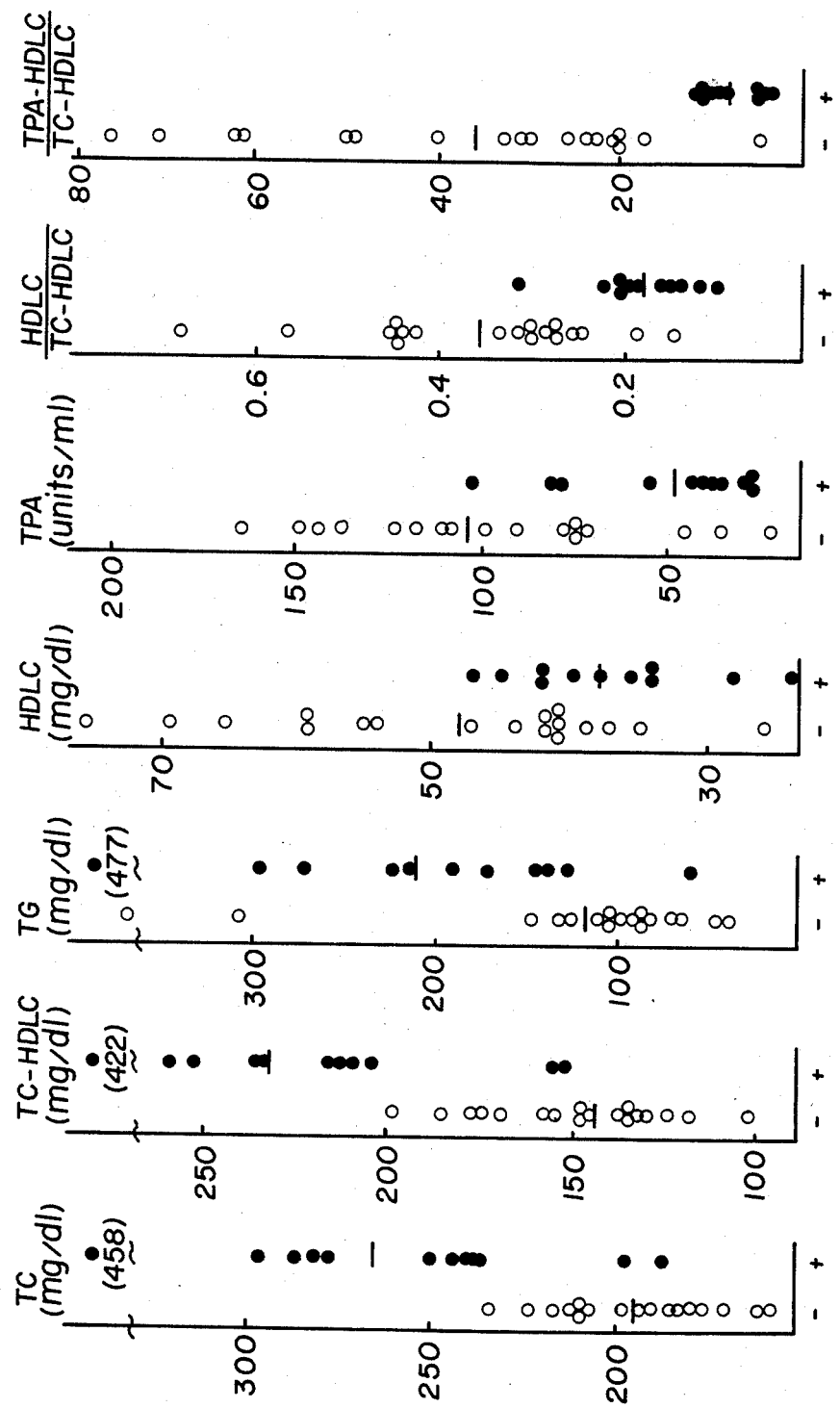

United States Patent [19]

Arbogast

[11] Patent Number: 4,699,878
[45] Date of Patent: Oct. 13, 1987

[54] PROCESS FOR THE DETERMINATION OF THE TOXICITY PREVENTING ACTIVITY OF HUMAN BLOOD SERUM

[75] Inventor: Bradley W. Arbogast, Johnson City, Tenn.

[73] Assignee: East Tennessee State University, Johnson City, Tenn.

[21] Appl. No.: 707,483

[22] Filed: Mar. 1, 1985

[51] Int. Cl.$^4$ .................... C12Q 1/60; C12Q 1/18
[52] U.S. Cl. .................................. 435/11; 435/4; 435/29; 435/32; 436/63; 436/71
[58] Field of Search .................... 435/29, 32, 4, 11; 436/63, 71

[56] References Cited

PUBLICATIONS

Chan et al (1978), Cancer Research, vol. 38, No. 9, pp. 2958–2961.
Soutar et al (1984), Biochemical Journal, vol. 218, No. 1, pp. 101–111.
Arbogast (1982), Diabetes vol. 31, No. 7, pp. 593–599 from Chemical Abstracts (1982) p. 451, vol. 97, No. 7, item No. 53534m.
Wu et al (1979), Artery, vol. 6, No. 5, pp. 385–401, from Chemical Abstracts (1980), vol. 93, No. 5, p. 653, item No. 43290g.
Chi et al (1982), Diebetes, vol. 31, No. 12, pp. 1098–10104, from Chemical Abstracts (1983), vol. 98, No. 5, p. 524, item No. 32885g.
In vitro Injury of Porcine Aortic Edothelial Cells by Very-Low-Density Lipoproteins from Diabetic Rat Serum, "Diabetes, vol. 31, No. 7, Jul. 82".
Injury of Arterial Endothelial Cells in Diabetic, Sucrose-Fed and Aged Rats, "Atheroclerosis 51 (1984), 31–45".

*Primary Examiner*—Sam Rosen
*Assistant Examiner*—William J. Herald

[57] ABSTRACT

A process for the determination of the toxicity preventing activity (TPA) of human blood serum, i.e., the effectiveness of the serum in preventing or inhibiting the destructive effect of very low density lipoproteins (VLDL) on test cells, and the use of this TPA value for classifying the serum as to atherosclerosis risk or potential. The process comprises:

(a) providing a culture of cells which are injured by elevated levels of VLDL;
(b) adding thereto a toxic quantity of VLDL and a selected quantity of human blood serum;
(c) maintaining the culture for a known period; and
(d) determining the cell growth of the culture and relating the same to the cell growth of a reference culture.

5 Claims, 3 Drawing Figures

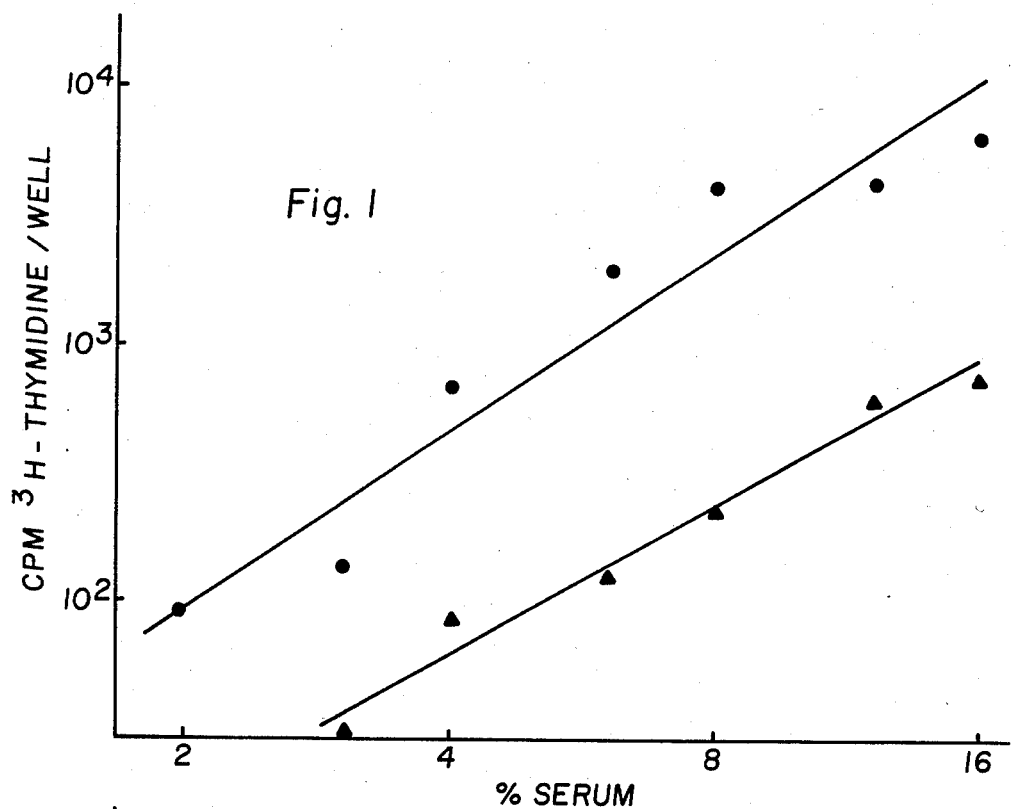
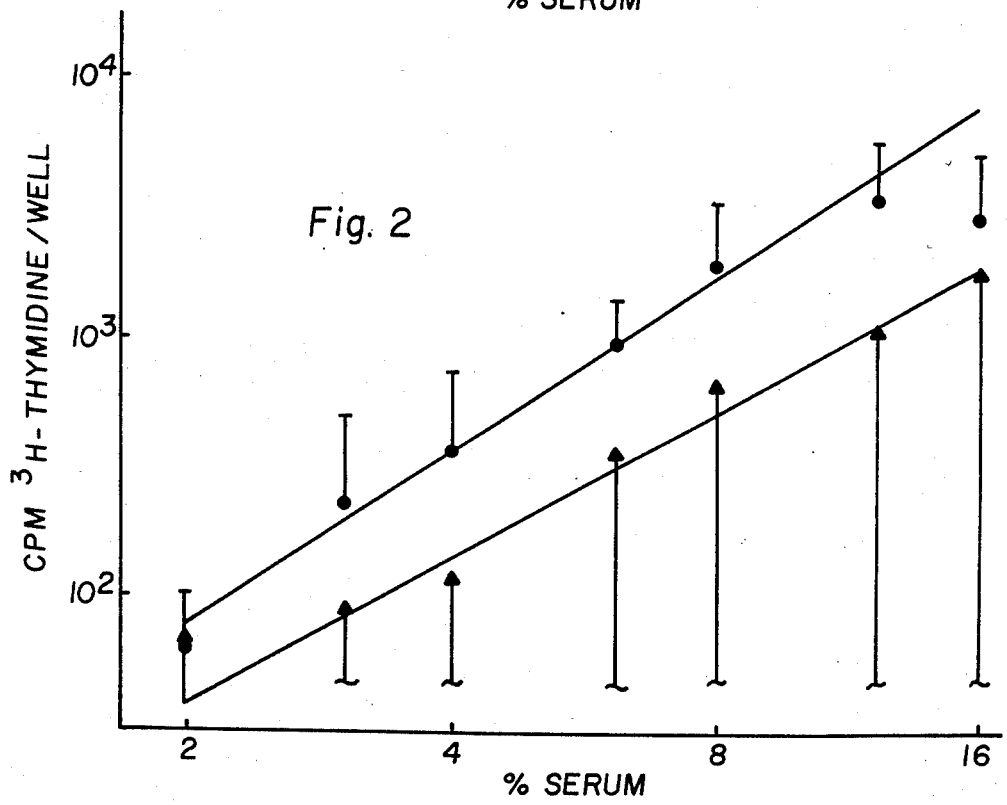

PROCESS FOR THE DETERMINATION OF THE TOXICITY PREVENTING ACTIVITY OF HUMAN BLOOD SERUM

This invention concerns a process for the determination of the toxicity preventing activity (TPA) of human blood serum, ie, the effectiveness of the serum in preventing or inhibiting the destructive effect of very low density lipoproteins (VLDL, $d < 1.006$ g/ml) on test cells, and the use of this TPA factor for classifying the serum as to atherosclerosis potential.

Atherosclerosis, which involves deterioration of the inner walls of arteries, has been long associated with cholesterol and other components in the blood such as high-density lipoprotein cholesterol (HDLC), triglycerides, and the like. Various techniques have been developed for measuring the levels of these components in the blood, however, a significantly reliable technique or process for relating these components and their levels to the incidence of or potential for atherosclerosis has not been forthcoming. The present invention essentially obviates the need for direct or even indirect association or correlation of such individual component levels to atherosclerosis risk or potential by the use of the newly discovered TPA factor either alone as an empirical estimation of the risk or potential, or in conjunction with, for example, other component levels in a mathematical relationship hereinafter described.

The present invention is defined in its broad sense as a process for determining the Toxicity Preventing Activity (TPA) of human blood serum in preventing cell destruction by VLDL, comprising:

(a) providing a culture of cells obtained from the vascular systems of pigs or cows which are injured by elevated levels of VLDL;
(b) adding thereto a toxic quantity of VLDL, and a selected quantity of human blood serum;
(c) maintaining the culture for a prescribed period, preferably from about 12 hours (h) to about 110 hours, and
(d) determining the cell growth of the culture and relating the same to the cell growth of a reference culture.

In regard to this process, it has been shown that in vivo and in vitro elevation of very-low-density lipoproteins (VLDL) in rat serum causes the whole serum to become toxic to porcine aortic endothelial cells in culture. See the published articles of Arbogast BW, Lee GM, Raymond TL, "In vitro injury of porcine aortic endothelial cells by very-low-density lipoproteins from diabetic rat serum," Diabetes 1982; 31: 593-599, and of Arbogast BW, Berry DL, Newell CL, "Injury of arterial endothelial cells in dia- betic, sucrose-fed and aged rats, Atherosclerosis 1984; 51: 31-45, both incorporated herein by reference for an in-depth disclosure of this phenomenon and particularly for a disclosure of the methods summarized below which can be employed in the present invention to prepare the porcine cell cultures and the VLDL, and of the use of statistics and scanning electron microscopy to evaluate or assay the toxocological effects of the VLDL.

PREPARATION OF CELL CULTURE

The intercostal arteries of fresh pig aortas are ligated with silk suture, a pinch clamp applied to one end of the aorta and the resulting cavity filled with 7-10 ml of a 1 mg/ml collagenase solution (type II, Worthington Biochemical Corp., Freehold, N.J.) in Medium 199 with Earle's Salts (Grand Island Biological Co., Grand Island, N.Y.), 2.2 g/L $NaHCO_3$, 2.5 ug/ml Amphotericin B (Grand Island Biological Co.) and 50 ug/ml gentamicin sulfate (Schering Corp., Kenilworth, N.J.). A pinch clamp is applied to the open end and the aorta incubated 40 min at room temperature. One end of the aorta is then cut off and the collagenase solution discarded. The aorta is rinsed four times with about 10 ml of a mixture of Medium 199 and fetal bovine serum (Grand Island Biological Co.) in a volume ratio of about 5/1. Rinses from 10-15 aortas are pooled and plated in 60-mm plastic tissue culture dishes (4 ml per dish). Cultures are switched to 2 ml of test media 24-48 hours after plating. All test media are filter sterilized through 0.22 Millex (Millipore Corp., Bedford, Me.) or 0.20 Nalgene filter units (Nalge Co., Rochester, N.Y.). Cultures are maintained at 37° C. in a humidified atmosphere (95% relative humidity) of 5% $CO_2$ in air.

PREPARATION OF VLDL

Blood obtained from streptozotocin-induced diabetic rats is allowed to clot for 1 h at 37° C. and then centrifuged at $300 \times$ g for 10 min at 4° C. to prepare serum (supernatant). The serum is then centrifuged in a SW-41 rotor in a Beckman L5-75B ultracentrifuge (Smith Kline-Beckman, Philadelphia, Pa.) at $175,000 \times$ g for 18 h at 4° C. The VLDL ($d < 1.006$ g/ml) fraction and the d°1.006 infranatant are separated using a tube slicer. The VLDL fraction is diluted with cold 0.15 M NaCl and given a wash spin a $175,000 \times$ g for 18 h at 4° C.

The serum and serum fractions are electrophoresed in 0.8% agarose gel and stained with oil red 0 to determine the electrophoretic mobility of the lipoproteins (Noble, R.P. Electrophoretic separation of plasma lipoproteins in agarose gel, J. Lipid Res. 9: 693, 1968). Normal rat serum is used as the standard. Triglycerides are assayed on a Sequential Multiple Analyzer 18 of Technicon, Tarrytown, NY (Bucolo, G. and Davis, H. Quantitative determination of serum triglycerides by use of enzymes. Clin. Chem. 19: 475, 1973).

ASSAY

To determine the toxicity of different serum fractions, 1- or 4-day primary cultures of porcine aortic endothelial cells are changed to test medium containing for example, each of VLDL, $d > 1.006$ infranatant, or whole serum. Cultures are continued 4 days and the plates then rinsed 3 times with Tyrode's solution (Tyrode, M. V. The mode of action of some purgative salts, Arch. Int. Pharmac. Therap., 20: 205, 1910) from Grand Island Biological Co., and the cells harvested in 2 rinses of 0.5 ml each of distilled water by scraping. Protein is measured according to the procedure of Lowry (Lowry, O. H., Rosebrough, N. J., Farr, A. L. and Randall, R. J. Protein measurement with the Folin phenol reagent. J. Biol. Chem. 193: 265, 1951), using bovine albumin Cohen Fraction V (Sigma Chemical Co.) as the standard.

STATISTICS

Statistical differences are determined using the Student test for paired means. A $P < 0.05$ is considered to be significant. Regression analyses is performed using the statistical program of a Hewlett-Packard 9815A computer. Confidence limits and significance of correlation are tested using standard procedures as described by Snedecor, G. W. and Cochran, W. G., Statistical Methods, Iowa State University Press, Ames, IA, 1967.

Referring back hereof concerning the toxification of rat serum by the in vivo elevation of VLDL, similar elevation of VLDL in human serum do not produce a serum which is toxic to endothelial cells in vitro. In our investigation of this discrepancy, VLDL samples which were isolated from both diabetic rat and type IV hyperlipemic human serum were added at elevated levels to both normal rat and nurmal human serum and incubated with endothelial cells in vitro. Both of the VLDL samples were found to be toxic in normal rat serum, but neither was toxic in normal human serum. Human serum, therefore, appeared to contain a factor which we designated TPA and which prevented or at least markedly diminished the toxicity of elevated levels of the VLDL. The effectiveness of the TPA or its value for an individual is visually observable with respect to allowing normal culture growth in the presence of the VLDL and can be used as a measure or estimate of the potential of the human source of the serum for developing artherosclerosis. This estimate can be made simply by visual comparison for each subject of the growth of cultures treated as above with his serum to those cultures for humans having 15% narrowing of coronary arteries (considered normal subjects).

The following is a guide for the use of TPA:
1. By itself as an indicator of protection against coronary artery disease;
2. Combined with other protective or risk factors in serum, plasma or blood (see below) to indicate presence or risk iof coronary artery disease wherein the ratio of the product of protective factors to risk factors provides a very acceptable classification for individuals with and without coronary artery disease.

Risk Factors:
Low-Density Lipoproteins (LDL);
Low-Density Lipoproteins (LDL)+VLDL;
Triglyceride (TG);
Total Cholesterol (TC);
VLDL;
Any combination of the above.

Protective Factors:
High-density Lipoproteins (HDL);
Toxicity Preventing Activity (TPA).

The definitions and characterizations of the above VLDL, LDL, HDLC, TC and TG are well known to the art as described in:

Havel R J, Eder H A, Bragdon J A. The distribution and chemical composition of ultracentrifugally separated lipoproteins in human serum. J. Clin Invest 1955; 34: 1345–1353, Clark D A, Rozell P R, Mosser E L. Evaluation of a kit to measure HDL cholesterol (HDL-C) in serum. Clin Chem 1983; 29: 1311, and Bucolo G, David H. Quantitative determination of serum triglycerides by the use of enzymes. Clin Chem 1973; 19: 476–482.

In the ratio $$\frac{TPA \times HDLC}{TC\text{-}HDLC}$$

described in detail below, the units for TC and HDLC are mg/dl (milligrams per deciliter). It is noted that HDLC is a substantially fixed portion of HDL and may be used as one means of quantifying HDL, but protein or TG concentrations could also be used.

The following references are available for further detailed information on materials and preparations employed herein:

Primary Cell Cultures

Arbogast B W, Lee G M, Raymond T L. In vitro injury of porcine aortic endothelial cells by very-low-density lipoproteins from diabetic rat serum. Diabetes 1982; 31: 593–599.

VLDL and HDL Preparation

Junod A, Lambert A E, Orci L, Piatet R, Gonet A E, Renold A E. Studies of diabetogenic action of streptozotocin. Proc Soc Exp Biol Med 1967; 126: 201–205. Havel R J, Eder H A, Bragdon J A. The distribution and chemical composition of ultracentrifugally separated lipoproteins in human serum. J Clin Invest 1955; 34: 1345–1353.

Koga S, Horowitz D L, Scanu A M. Isolation and properties of lipoproteins from normal rat serum. J Lipid Res 1969; 19: 577–588.

Medium 199

Morgan J F, Morton H G, Parker R C. Nutrition of animal cells in tissue culture. AI. Initial studies on a synthetic medium. Proc Soc Exp Bio Med 1950; 73: 1–8.

In order to determine the level of TPA in 29 relatively young men (mean age=43±8 yr) who had undergone coronary angiography, an assay using the incorporation of tritiated thymidine into cultured endothelial cells was developed. Using values of TPA derived from this assay, total cholesterol (TC) and HDLC, a ratio of protective to risk factors $$\left[\frac{TPA \times HDLC}{TC\text{-}HDLC}\right]$$

was calculated which accurately classified 97% of the individuals.

METHODS

Subject Population

The subject population consisted of 29 men (age 43±8 yr) who had undergone coronary angiography using the Judkins technique. Left ventriculograms were obtained in the 30° right anterior oblique projection and selective coronary angiograms were performed in multiple projections. Subjects undergoing catheterization had either abnormal exercise tests, significant arrhythmia, valvular disease or left bundle block. Angiographic data were reviewed independently by two cardiologists and interpreted without knowledge of laboratory tests results. Individuals with 15% or less narrowing were considered normal while those having greater than 15% narrowing were classified as having coronary artery disease. None of the subjects had electrocardiographic evidence of a previous myocardial infarction and less than 10% had suspected or definite angina. No subject had hypertension that required any medication other than hydrochlorothiazide and none had diabetes mellitus.

Total serum cholesterol and HDLC were measured on fasting serum samples using an ABA-100 bichromatic analyzer (Abbott Laboratories, North Chicago, Ill.) with BMC Autoflor cholesterol reagents (Cat. No. 148393, Biodynamics/bmc, Indianapolis, IN). Triglycerides were enzymatically measured using the Stat-Pack Enzymatic Triglyceride (Cat. No. 869262, Calbiochem-Behring, LaJolla, CA) procedure.

Cell Culture

A 40-min collagenase digestion was used to obtain primary cultures of porcine thoracic aortic endothelial cells. The endothelial cells in Medium 199 (10) with Earle's Salts (Grand Island Biological Co., Grand Island, NY), 2.2 g/l NaHCO$_3$, 2.5 µg/ml Amphotericin B (Grand Island Biological Co.a), 50 µg/ml gentamicin sulfate (Schering Corp., Kenilworth, NJ) and 17% fetal bovine serum (Grand Island Biological Co.) were aliquoted into either 30-mm plastic tissue culture dishes (3 ml/dish, Falcon, Oxnard, CA), or MicroTest II tissue culture plates (200 µl/well, Falcon). Cultures were maintained at 37° C. in a humidified atmosphere (95% relative humidity) of 5% CO$_2$ in air. Only primary cultures were used.

Eighteen to 24 hours after plating the cultures were rinsed three times in Medium 199 and changed to medium containing the serum to be tested. Cells were then cultured for three days in the MicroTest II plates or 4 days in the 30-mm dishes. Cells were harvested from the 30-mm dishes as previously described and protein measured. Cells from the MicroTest II plates were collected on glass fiber filter paper using a Mash II Cell Harvester (Microbiological Associates, Inc., Walkersville, MD). Decreases in the amount of protein/dish were initially used to quantitate VLDL toxicity. A microassay using tritiated thymidine incorporation was then developed and used to quantitate VLDL toxicity in the latter stages of the research.

VLDL were prepared from either type IV hyperlipemic human or diabetic Spraque-Dawley rats as previously described. HDL were sprayed from normal human serum sequential density by flotation in a Beckman L5-75B ultracentrifuge with an SW-41 rotor (Smith Kline-Beckman, Philadephia, PA). Lipoproteins were electrophoresed in 0.8% agarose gel and stained with oil red 0 to confirm type IV hyperlipemia, and to assess the purity of the VLDL fractions.

TPA Assay

To quantitate the amount of TPA, 16% serum in Medium 199 was serially diluted with Medium 199 to obtain concentrations of 1, 2, 3, 4, 6, 8, 12 and 16 percent serum. Fifty microliters of these dilutions were then transferred to separate wells of a MicroTEst II plate containing 1 day old primary cultures of porcine aortic endothelial cells. A mixture of diabetic rat VLDL (0.90 mg triglyceride/ml) and thymidine [methyl-$^3$H], (1.0 µCi/ml, New England Nuclear, Boston, MA, 6.7 Ci/mmole) in Medium 199 (50 µl) was then added to each well and the cells cultured for three more days.

A power regression ($y = ax^b$; y=cpm, x=percent serum) provided the best fit of the data and was used to calculate values of a and b for each serum. The mean regression line for the group of 18 subjects who had less than 15% narrowing of their coronary arteries was then calculated and given the arbitrary value of 100 units. Horizontal shifts of the individual serum regression lines from this mean normal regression line were then calculated at 12% serum for each of the 29 serum samples using the a and b values obtained from their individual regression analysis. This analysis provided a quantitative measurement of the TPA in the individual sera. For example, a serum for which the regression line ran through the points x=6% serum, y=1000 cpm would have twice as much TPA as serum for which the regression line ran through x=12% serum, y=1000 cpm.

Statistics

Data are reported as mean±standard deviation. Statistical differences were determined using Student's t test for paired means. A value of P<0.05 was considered to be significant. Regression analyses were performed using the statistical program of a Hewlett-Packard 9815A computer.

RESULTS

In Table 1, VLDL were isolated from diabetic rat and type IV hyperlipemic human serum and added to either 17% normal rat or 17% normal human serum. At elevated levels (500 mg/dl serum) both rat and human VLDL in rat serum were toxic to porcine aortic endothelial cells as noted by the reduced amounts of protein/dish. However, neither was toxic in the presence of 17% human serum. Human serum, therefore, contained a substance (TPA) which protected against the toxicity of elevated levels of both human and rat VLDL.

Since HDLC is a negative risk factor in coronary artery disease, and since it has been reported to reverse LDL toxicity in vitro, its relationship to TPA was examined. Ultracentrifugation of normal human serum revealed that the protective activity sedimented at a density greater than 1.225 g/ml (Table 2). Likewise, addition of purified HDL (1.063<d<1.225) at concentrations up to 5 times normal did not result in an increased amount of protein/dish and thus ruled out the possibility that HDL alone was the protective activity in this assay.

A semiquantitative biological assay was then developed to measure the level of this VLDL Toxicity-Preventing-Activity (TPA) in serum. FIG. 1 demonstrates curves obtained from two different human sera, one having a high (●) and ione having a low (▲) level of TPA. The correlation coefficients for the two lines were 0.96 and 0.99 respectively. The high activity serum had 117 units of TPA while the low activity serum contained 37 units.

This assay was then used to measure TPA in 29 male subjects who had undergone coronary angiography. FIG. 2 shows a log-log plot of the mean±SD of the counts per minute of the two groups at each of the serum dilutions. All serum samples were analyzed with the same pool of endothelial cells on the same day. Subjects with coronary artery disease had approximately half as much TPA (48±24 units) as those without coronary artery disease (104±48 units). Only points in the linear portion of the curves were used to calculate the regression lines. The slopes of the two lines are not statistically different, however, the elevations are significantly different at the p<0.001 level.

The mean regression line for the group of sera from individuals with less than 15% narrowing was assigned an arbitrary value of 100 units and individual values of TPA were calculated from this line as described in the Methods section. These results, as well as the age, total cholesterol (TC), triglyceride (TG) and high-density lipoprotein cholesterol (HDLC) values are shown in Table 3. All of the differences between the two groups were statistically significant, except for the ages. When the two negative risk factors (TPA and HDLC) are multiplied together and divided by the non-HDLC, a significant difference is established (p<0.001). In this instance (the last column), there is almost complete separation between the two groups. One individual out of 29 (3%) is misclassified by this calculation.

Two individuals in the coronary artery disease group with total cholesterol levels below 200 mg/dl (subjects 21 and 24, Table 3) would normally be classified as low to average risk by several standard criteria (TC, HDLC, TG, TC to HDLC ratio). However, when their low levels of TPA (35 and 43 respectively) are considered, one can, for the first time, place them into the coronary artery disease group. Conversely, the two individuals in the group without coronary artery disease who have the highest cholesterol values (subjects 11 and 15) would normally be expected to be in the high risk group. The apparent explanation for their lack of coronary artery disease may well be the high levels of TPA (123 and 145 units respectively) in these two individuals. Thus, the combination of the two protective factors, HDLC and TPA, and the risk factor, non-HDLC, yields a ratio which correlates with 97% of the coronary artery disease in this group of individuals.

TABLE 1
Toxicity of VLDL in Human and Rat Serum

|  | μg Protein/Dish |
|---|---|
| Rat Serum | 172 ± 34 |
| Rat Serum + Rat VLDL | 40 ± 14 |
| Rat Serum + Human VLDL | 70 ± 5 |
| Human Serum | 181 ± 20 |
| Human Serum + Rat VLDL | 183 ± 18 |
| Human Serum + Human VLDL | 190 ± 16 |

Diabetic rat or Type IV hyperlipemic human serum was used to prepare washed rat and human VLDL. Rat or human VLDL (500 mg triglyceride/dl serum) were then added to either 17% normal rat or 17% normal human serum in Medium 199. These media were added to 1-day cultures of porcine aortic endothelial cells and culture continued 4 days. The cells were then harvested and assayed for protein. Each value represents the mean±standard deviation of triplicate cultures. Rat serum containing either rat or human VLDL was significantly different from rat serum alone (p<0.001) while human serum with either rat VLDL or human VLDL was not significantly different from human serum alone.

TABLE 2
Effect of HDL on VLDL Toxicity

| Additions | μg Protein/Dish |
|---|---|
| None | 145 ± 36 |
| Rat VLDL | 35 ± 9 |
| Rat VLDL + Human Serum (d < 1.225 g/ml) | 26 ± 6 |
| Rat VLDL + Human Serum (d > 1.225 g/ml) | 136 ± 46 |
| Rat VLDL + Human HDL (1.063 < d < 1.225) | 45 ± 8 |

Diabetic rat VLDL, lipoproteins from normal human serum (d<1.225 g/ml), lipoprotein deficient serum (d>1.225 g/ml) and human HDL (1.063 g/ml<d<1.225 g/ml) were added separately to Medium 199 containing 17% normal rat serum. Rat VLDL was present at a concentration of 500 mg triglyceride/dl serum, the human lipoprotein fraction (d<1.225 g/ml) and the lipoprotein deficient serum fraction (d>1.225 g/ml) were present at concentrations equivalent to 17% serum and human HDL was present at a concentration 5 times that found in the normal serum. These media were added to 1-day endothelial cells and culture continued 4 days. The cells were harvested and assayed for protein. Each value represents the mean±SD of triplicate cultures. The media containing rat VLDL, rat VLDL+Human d<1.225 g/ml and rat VLDL+human HDL are statistically significant from the 17% rat serum control (none). Cells cultured in media containing rat VLDL and Human d>1.225 g/ml) were not significantly different.

TABLE 3
Individual Lipoprotein and Toxicity Preventing Activity Levels in Men Who Had Undergone Coronary Angiography

|  | Patient | Age (yr) | TC (mg/dl) | TC-HDLC (mg/dl) | TG (mg/dl) | HDLC (mg/dl) | TPA (Units/ml) | HDLC/TC-HDLC | TPA HDLC/TC-HDLC |
|---|---|---|---|---|---|---|---|---|---|
| No Coronary Artery Disease (<15% narrowing) | 1. | 37 | 210 | 184 | 367 | 26 | 33 | 0.14 | 4.7 |
|  | 2. | 49 | 174 | 133 | 101 | 41 | 99 | 0.31 | 30.5 |
|  | 3. | 35 | 160 | 123 | 128 | 37 | 76 | 0.30 | 22.9 |
|  | 4. | 43 | 170 | 101 | 39 | 69 | 111 | 0.68 | 75.8 |
|  | 5. | 53 | 191 | 147 | 103 | 44 | 79 | 0.30 | 23.6 |
|  | 6. | 44 | 179 | 124 | 84 | 55 | 90 | 0.44 | 39.9 |
|  | 7. | 38 | 215 | 174 | 102 | 41 | 73 | 0.24 | 17.2 |
|  | 8. | 48 | 197 | 155 | 93 | 42 | 76 | 0.27 | 20.6 |
|  | 9. | 22 | 182 | 128 | 55 | 54 | 167 | 0.42 | 70.4 |
|  | 10. | 52 | 217 | 158 | 128 | 59 | 110 | 0.45 | 49.3 |
|  | 11. | 54 | 224 | 177 | 87 | 47 | 123 | 0.27 | 32.7 |
|  | 12. | 50 | 185 | 144 | 87 | 41 | 214 | 0.28 | 60.9 |
|  | 13. | 38 | 192 | 133 | 91 | 59 | 139 | 0.44 | 61.7 |
|  | 14. | 40 | 209 | 134 | 47 | 75 | 36 | 0.56 | 20.2 |
|  | 15. | 48 | 234 | 199 | 308 | 35 | 145 | 0.18 | 25.5 |
|  | 16. | 38 | 158 | 119 | 69 | 39 | 150 | 0.33 | 49.2 |
|  | 17. | 42 | 210 | 168 | 147 | 42 | 118 | 0.25 | 29.5 |
|  | 18. | 46 | 213 | 148 | 112 | 65 | 46 | 0.44 | 20.2 |
| Mean ± SD |  | 43 ± 8 | 195 ± 22 | 147 ± 26 | 119 ± 85 | 48 ± 13 | 104 ± 48 | 0.35 ± 0.14 | 36.3 ± 20.4 |
| Coronary Artery Disease (>15% narrowing) | 19. | 47 | 286 | 252 | 223 | 34 | 26 | 0.14 | 3.5 |
|  | 20. | 43 | 276 | 234 | 216 | 42 | 55 | 0.18 | 9.9 |
|  | 21. | 37 | 198 | 151 | 62 | 47 | 35 | 0.31 | 10.9 |
|  | 22. | 42 | 251 | 209 | 272 | 42 | 26 | 0.20 | 5.2 |
|  | 23. | 40 | 240 | 212 | 477 | 28 | 84 | 0.13 | 11.1 |
|  | 24. | 45 | 187 | 153 | 144 | 34 | 43 | 0.22 | 9.6 |
|  | 25. | 42 | 458 | 422 | 191 | 36 | 103 | 0.09 | 8.8 |
|  | 26. | 48 | 297 | 259 | 129 | 38 | 82 | 0.15 | 12.0 |
|  | 27. | 46 | 244 | 204 | 172 | 40 | 41 | 0.20 | 8.0 |
|  | 28. | 41 | 278 | 233 | 296 | 45 | 29 | 0.19 | 5.6 |
|  | 29. | 44 | 237 | 213 | 145 | 24 | 37 | 0.11 | 4.2 |

TABLE 3-continued

Individual Lipoprotein and Toxicity Preventing Activity Levels in Men Who Had Undergone Coronary Angiography

| Patient | Age (yr) | TC (mg/dl) | TC-HDLC (mg/dl) | TG (mg/dl) | HDLC (mg/dl) | TPA (Units/ml) | $\dfrac{HDLC}{TC\text{-}HDLC}$ | $\dfrac{TPA\ HDLC}{TC\text{-}HDLC}$ |
|---|---|---|---|---|---|---|---|---|
| Mean ± SD | 43 ± 3 | 266 ± 68 | 231 ± 72 | 211 ± 110 | 38 ± 7 | 48 ± 24 | 0.17 ± 0.06 | 8.1 ± 3.0 |
| P< | N.S. | 0.001 | 0.001 | 0.025 | 0.025 | 0.001 | 0.001 | 0.001 |

TC = Total serum cholesterol, TC-HDLC = non-HDL cholesterol, TG = Triglyceride, HDLC = High-density lipoprotein cholesterol, TPA = Toxicity preventing activity.

LEGENDS FOR ILLUSTRATIONS

FIG. 1—Measurement of Toxicity Preventing Activity in Serum from Two Individuals FIG. 2—Toxicity Preventing Activity in Serum from Individuals with (●) and without (▲) Angiographically Documented Coronary Artery Disease.

FIG. 3—Risk and Protective Factors in Men Who Had Undergone Coronary Angiography.

DISCUSSION

These results indicate that 97% of the individuals with angiographically demonstrable coronary artery disease can be accurately identified based upon the clinical analysis of three serum components. Two of these components, HDLC and non-HDLC, have previously been correlated with the presence of coronary artery disease. However there have always been a number of individuals who have been misclassified using only these two criteria, severely limiting the usefulness of these determinations when applied to individual patients (5, Table III). Only when the TPA values are included in the formula (FIG. III) do the subjects separate into two distinct groups. The rationale for using this evaluation is based upon the observation that HDLC and TPA are both inversely correlated with coronary artery disease while non-HDLC is positively correlated with coronary artery disease. Thus this particular ratio, $$\frac{TPA \times HDLC}{TC\text{-}HDLC},$$

provides the greatest separation of the groups.

With the identification of TPA and the increased power of classification that it adds to the HCLC/TC-HDLC ratio, one may now be able to accurately and easily assess coronary artery disease risk in man. This accuracy in prediction should lead to more rigorous treatment of those individuals in the high risk group. Drugs, diet and exercise regimens can be designed which will shift individuals from the high risk to low risk group. Because of the ease and speed of determining the levels of these serum factors compared with the current methods of assessing the presence of coronary artery disease in humans, the development of new treatments should proceed rapidly.

The invention has been described in detail with particular reference to preferred embodiments thereof, but it will be understood that variations and modifications can be effected within the spirit and scope of the invention.

I claim:

1. A process for determining the toxicity preventing activity (TPA) of human blood serum in preventing cell destruction by very low density lipoprotein, (VLDL) comprising:
   (a) providing a culture of cells which are injured by elevated levels of VLDL;
   (b) adding thereto a toxic quantity iof VLDL and a selected quantity of human blood serum to be tested;
   (c) maintaining the culture for a period of time sufficient to inhibit cell growth in the absence of TPA;
   (d) determining the cell growth of the culture and relating the cell growth to the cell growth of a reference culture; and
   (e) calculating the TPA from the magnitude of horizontal shifts iof an individual's serum regression lines from a standard regression line.

2. The process of claim 1 wherein the cells are obtained from the vascular systems of pigs or cows.

3. The process of claim 2 wherein the VLDL is obtained from rats or humans.

4. The process iof claim 1 wherein the TPA, high density lipoprotein cholesterol (HDLC), and total cholesterol (TC) are used according to the equation $$\frac{TPA \times HDLC}{TC\text{-}HDLC}$$

to classify the individual.

5. The process of claim 1 wherein tritiated thymidine is employed to quantitate the cell growth.

* * * * *